(12) United States Patent
Doubler et al.

(10) Patent No.: US 6,551,323 B2
(45) Date of Patent: Apr. 22, 2003

(54) METHOD OF MAKING A BONESCREW

(75) Inventors: Robert L. Doubler, Ida, MI (US); John E. Hammill, Sr., Rossford, OH (US); Jeffrey Lasner, Purchase, NY (US)

(73) Assignee: Hammill Manufacturing, Toledo, OH (US)

( * ) Notice: Subject to any disclaimer, the term of this patent is extended or adjusted under 35 U.S.C. 154(b) by 0 days.

(21) Appl. No.: 09/915,775

(22) Filed: Jul. 26, 2001

(65) Prior Publication Data

US 2001/0047175 A1 Nov. 29, 2001

Related U.S. Application Data

(62) Division of application No. 09/524,791, filed on Mar. 14, 2000, now Pat. No. 6,375,657.

(51) Int. Cl.$^7$ .............................................. A61B 17/86
(52) U.S. Cl. .......................................... 606/73; 470/10
(58) Field of Search .................... 470/8, 9, 10; 82/1.11; 606/61, 73

(56) References Cited

U.S. PATENT DOCUMENTS

| 5,120,171 A | | 6/1992 | Lasner |
| 5,221,234 A | * | 6/1993 | Pakos ........................... 470/10 |
| 5,226,766 A | | 7/1993 | Lasner |
| 5,417,533 A | | 5/1995 | Lasner |
| 5,492,442 A | | 2/1996 | Lasner |

* cited by examiner

*Primary Examiner*—David O. Reip
(74) *Attorney, Agent, or Firm*—McHale & Slavin PA

(57) ABSTRACT

A screw for use in spinal and other surgical procedures has a tapered core and fixed pitch threads. The threads have a compound curved inferior surface and constant width crest. The screw may be provided with a helical thread in which at least the lead thread adjacent to the screw tip is ledged and the following threads have sharp apices. A method of making the screw requires two tool bits making two different angular cuts to the inferior surface of the threads.

1 Claim, 8 Drawing Sheets

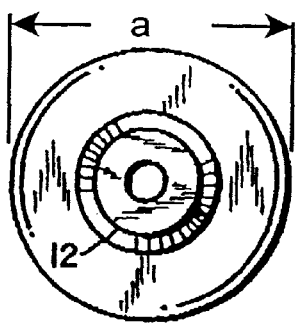
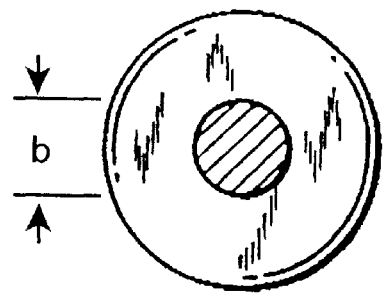
FIG. 3     FIG. 4
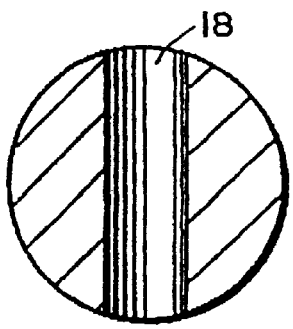
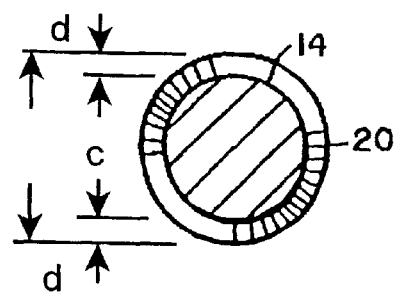
FIG. 5     FIG. 6
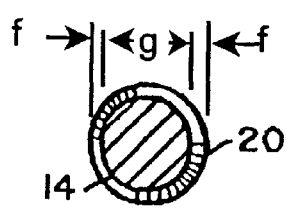
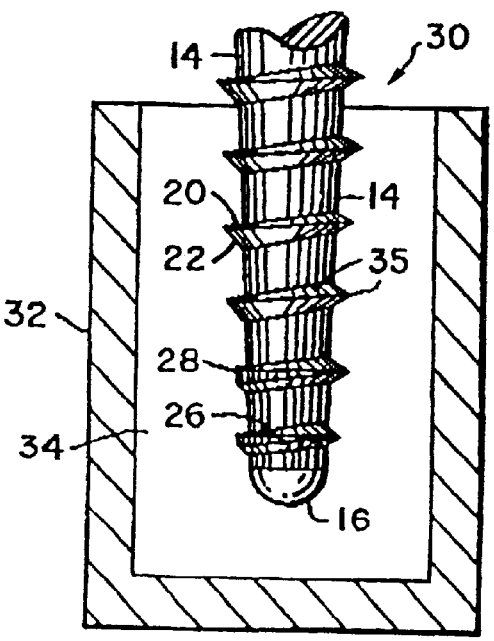
FIG. 7     FIG. 8

METHOD OF MAKING A BONESCREW

This application is a division of application Ser. No. 09/524,791 filed Mar. 14, 2000, now U.S. Pat. No. 6,375,657.

FIELD OF THE INVENTION

The present invention is directed to improved screws adapted to be inserted into bone and a method of making such screws.

BACKGROUND OF THE INVENTION

The present invention relates to a screw for use in spinal pathologies, deformities and trauma. Because of manufacturing restrictions, the currently available bone screw is not ideal since it is a screw having a tapered core with a constant thread diameter, but with thread apices adjacent to the screw head that are ledged or flattened near the head.

In order to correct spinal conditions spinal bone screws are loaded with axial, distractive and compressive forces and with subsequent cyclically loaded forces applied through the patients natural movement. The bone screws are typically inserted in the vertebral pedicle at a location which has a reduced thickness, or isthmus, midway along its length, and about half way between the posterior bony complex and the thicker vertebral body known as the pedicle.

Previously known bone screws required a relatively large core diameter in order to resist all forces on the screw and to permit the screw to have an uncompromised retention in the pedicle, while at the same time the screw required a minor diameter small enough so that the application will not force a split of the pedicle from the inside causing a condition commonly referred to as "blow out" of the pedicle.

Prior art attempts have been made to manufacture a bone screw that has a tapered core with a constant thread diameter while maintaining consistently sharp threads along the entire length of the screw, such as shown in U.S. Pat. No. 5,492,442 issued on Feb. 20, 1996. In practice, the manufacture of the bone screw having a tapered screw core and a constant thread diameter resulted in sharp threads starting from the pointed tip of the screw and advancing along the length of the screw with the last few threads adjacent to the thickest part of the core being ledged or flattened. This produces a situation in which the sharp threads created by the lead thread at the tip of the screw and the threads thereafter are corrupted by the last two or three threads that are ledged or flattened. The result is that the bone becomes microscopically fractured which lessens the pullout resistance of the screw for the bone. The function of the ledged threads on the screw is analogous to a log splitter being used to split a log.

SUMMARY OF THE INVENTION

The present invention is directed to improved screws adapted to be inserted into bone and a method of making such screws. The bone screws have a tapered core which is smaller at the leading end and larger at the head. The screw threads have sharp apices, and a constant pitch throughout the length of the screw. The screw has a constant outside diameter throughout the length.

One embodiment of the bone screw has concave superior thread surfaces and ledged threads at the leading end to prevent misalignment during placement. A tap is used in connection with the bone screw attachment.

A second embodiment has flat superior thread surfaces and a constant thread crest throughout the length of the screw. This embodiment may also have ledged threads at the leading end.

The method of making the screw requires process steps including a first tool bit for the initial thread formation and a second tool bit for refining the first set of threads to a constant crest width. The ledged leading threads may be formed at the beginning of the process, between the first and second tool bit, or as an after treatment.

Accordingly, it is an objective of the present invention to provide an improved tapered spinal bone screw having ledged or flattened threads at the beginning of, or lead threads, and in which the following threads have sharp apices, and that the area between threads or thread pitch is constant throughout the length of the threads.

It is another objective of the present invention to provide an improved tapered spinal bone screw having sharp apices along the entire length.

Still another objective of the present invention is the use of a tap in connection with pedicle screw placement. The use of tap alone without altering the bone screw construction could result in serious problems due to the possibility of cross-threading of the screw when introducing the screw into the bone, which consequently alters the path of insertion, that has been established by the tap. If the path is violated or corrupted, serious neurological problems can occur due to the close proximity of the spinal cord. In order to avoid this happening the lead threads of the screw each have a diameter less than the tap core, therefore the tip and some of the following threads of the screw will drop into the hole created by the tap, thus serving as a pilot hole whereby the path of insertion may be maintained, and thus effectively eliminating the possibility of cross threading.

Yet an additional important objective of the present invention to provide an improved spinal bone screw that can be manufactured with present conventional technology.

The screw is provided with a thread configuration, which anchors the screw to the bone and prevents the screw from being axially pulled out from the bone.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 3 is a cross-section view taken along the lines 3—3 of FIG. 1.

FIG. 4 is a cross-section view taken along the lines 4—4 of FIG. 1.

FIG. 5 is a cross-section view taken along the lines 5—5 of FIG. 1 and through the bore in the bone screw.

FIG. 6 is a cross-section view taken along the lines 6—6 of FIG. 4.

FIG. 7 is a cross-section view taken along the lines 7—7 of FIG. 1 and near the tip of the screw.

FIG. 8 is a side view showing the screw of our invention being threaded into a bone.

DETAILED DESCRIPTION OF THE INVENTION

Orthopedic surgeons, as well as neurosurgeons, have long recognized the need for screws in the treatment of spinal pathologies, deformities and traumas. The screws were placed in the vertebral pedicle 42 because this area has been long recognized as the "force nucleus" of the spinal vertebra. In other words, the area of the spine where a force applied to the bone by means of a screw would have the highest mechanical advantage in repositioning the bone. The present improved bone screw can also be used effectively by a surgeon in other procedures, such as anchoring tissue or in bone plating systems.

Referring particularly to FIGS. 1–9 a bone screw is shown which is fabricated of a well known biocompatible material such as stainless steel or titanium and has a screw-threaded head 12 and a cylindrical tapered core 14 having a tip 16 remote from the screw head. It should be noted that the screw core has the smallest diameter at its tip, and diameter of the core gradually increases toward the screw head.

Figure 1:
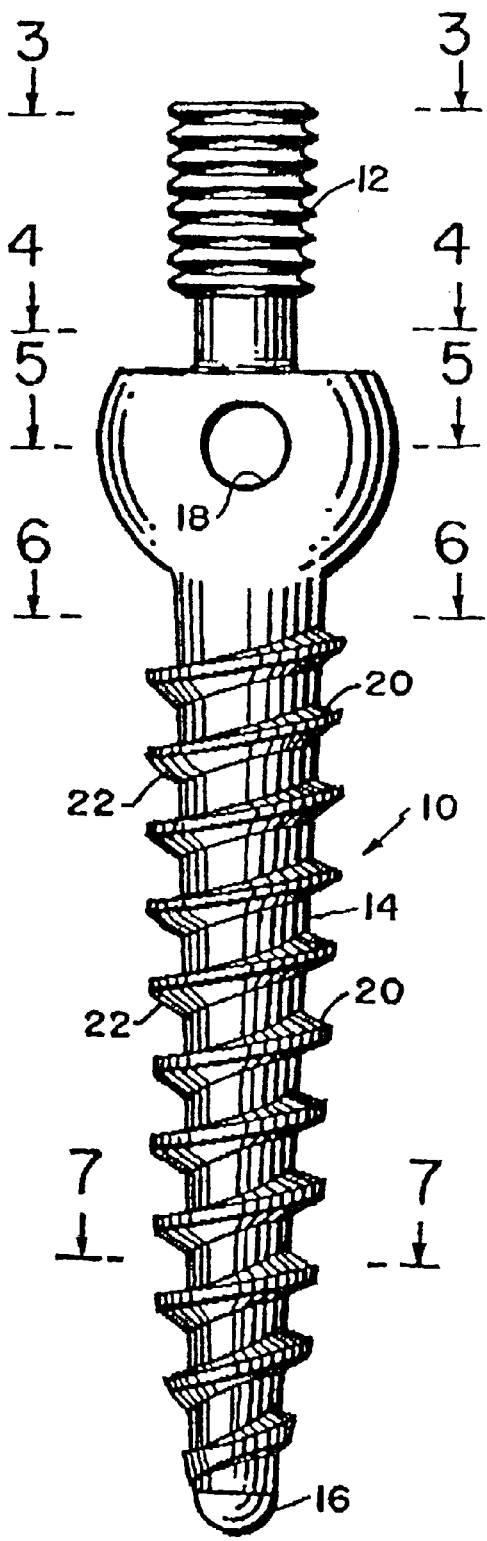
FIG. 1 is a front elevation of a bone screw constructed in accordance with the teachings of our invention.
Figure 2:
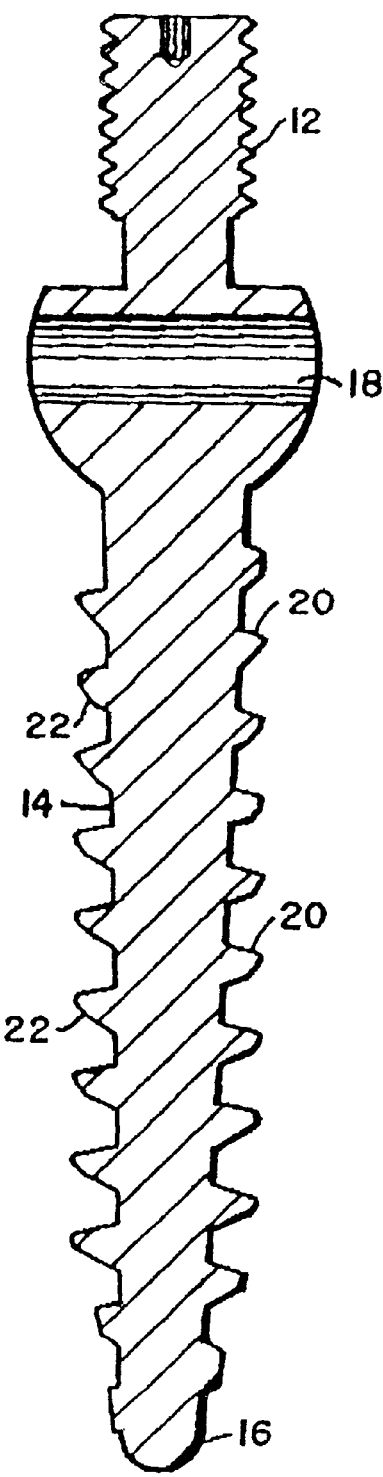
FIG. 2 is a longitudinal sectional view of the screw shown in FIG. 1.
Figure 9:
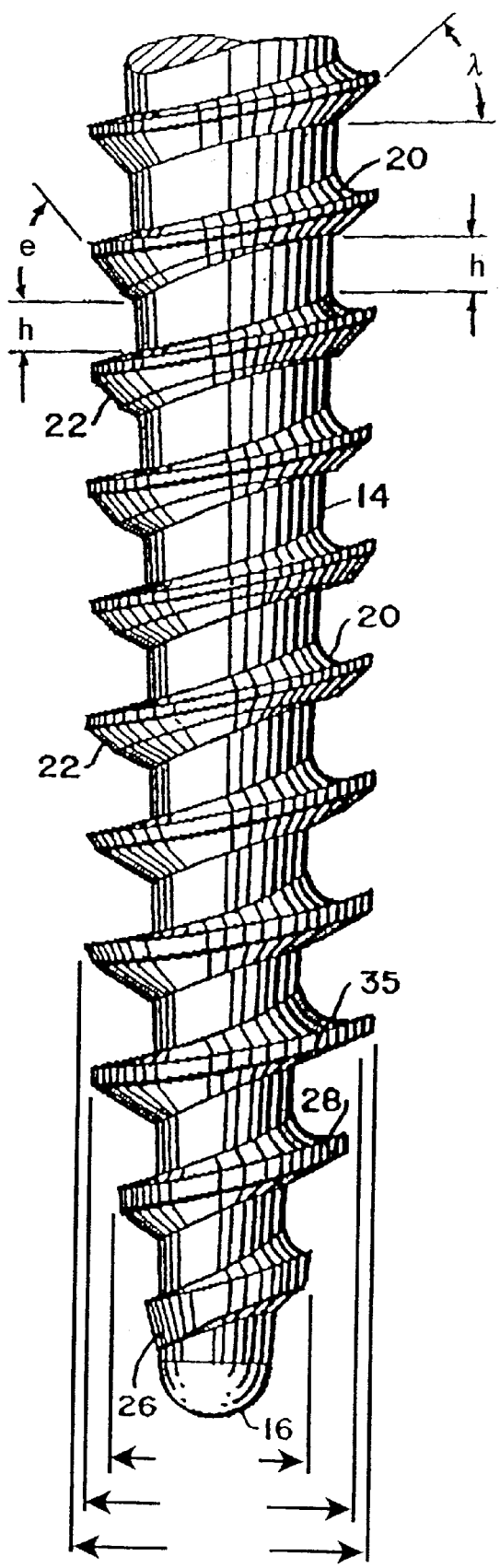
FIG. 9 is an enlarged front elevation view of the tapered, cylindrical, shaped core with its helical shaped screw threads.

The screw 10 is provided with a bore 18 through which a rod (not shown) is placed in order to support the spine. Each thread of the helical, ribbon-like thread on the core 14 has a superior surface 20 and an inferior surface 22. As seen in FIG. 9, which is an enlarged view of the bone screw, each of the superior surfaces 20 of the screw are concave, while the inferior surfaces 22 of each screw are of different angles, such as e and lambda.

In FIG. 3, the dimensions a shows the width of the screw heads as viewed from the top of the screw. FIG. 4 shows the dimension b taken through the lines 4—4 of FIG. 1. In FIG. 6, the inside diameter (ID) of the screw thread is shown at c while the outside diameter (OD) of the screw thread is shown at d. It should be noted that the thickness of the screw thread in FIG. 7 at the right hand side is somewhat thicker than the thickness of the screw thread at the left-hand side. The inside diameter (ID) of the screw thread is shown as g while the outside diameter (OD) is shown as f.

The distance between the threads, as seen in FIG. 9, is constant, as indicated by the reference letter h. However, the area between the threads decreases from the lead end toward the head. As seen in FIGS. 1, 2, 8 and 9, the lower two screw threads 26 and 28 adjacent to the screw tip 16 are ledged or flattened.

In utilizing the present bone screw for the purpose intended, the screw is inserted into the bone 30. The bone may have a tapped or untapped hole formed therein as a guide for the placement of the screw. In some cases the bone screw may be self-tapping.

The bone has a relatively hard compact shell 32, which encases a loose spongy cancellous bone material 34. While the screw of this invention is especially suited for use in bones, the advantages of the thread construction would apply to other materials with a hard shell and compressible interior.

Referring especially to FIG. 9, the ledged screw threads, as well as the following screw thread 32, have varying diameters, for example, screw thread 26 can be 7.75 mm in diameter, while screw thread 28 is slightly larger at 8.0 mm. Screw thread 35 can be even larger at 8.75 mm.

The present invention prevents the possibility of cross threading of the screw by using a tap previously established in the pedicle whereby the path of insertion is positively established, and together with the screw tip having ledged threads, the path is firmly maintained and no violation, or corruption, of the path is possible. It should be kept in mind that if the path of insertion is violated the screw assumes the position as seen in dotted lines in FIG. 17 . If this occurs serious neurological conditions can occur for a patient, due to the close proximity of the spinal cord.

Figure 11:
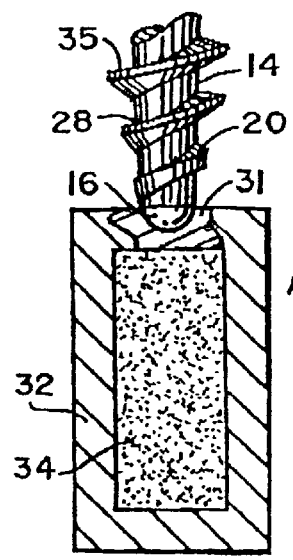
FIGS. 11–13 are side views showing the preferred embodiment of our invention being applied to a bone.
Figure 12:
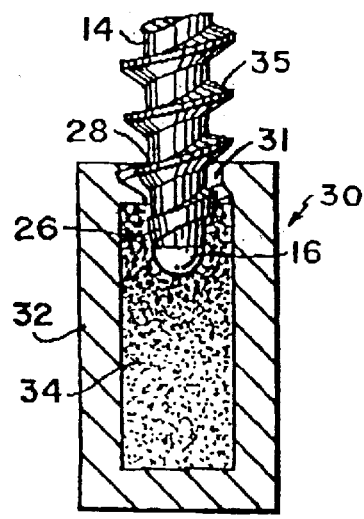
Figure 13:
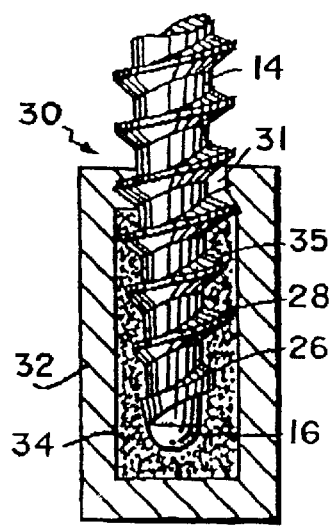

As seen in FIGS. 11–13, the screw 10 is shown rotated into the bone 30. However, prior to screwing the bone screw into the bone of the pedicle 42 the bone is tapped at 31 with a tap through the compact shell 32 into the cancellous material 34. In the embodiment shown for example, the tap diameter is 8.5 mm. The tap hole therefore forms a precise, preset path of insertion for the bone screw. Since the first ledged screw thread adjacent to the tip has a diameter of 7.75 mm; and the second following screw thread has a diameter of 8.0 mm, it is not until the third following thread 35 engages the threads of the tap and bites into the threads of the tapped hole that the path of insertion is established. In the area of thread 35 the tapered screw has an outside diameter of approximately 8.75 mm which is larger than the diameter of the tap. Consequently, the first two screw threads drop into the preset pilot hole formed by the tap, thus accurately positioning the screw to eliminate altering of the path of insertion, and reducing the possibility of cross-threading of the screw.

The remainder of the following screw threads also have larger diameters than the tap and are provided with sharp apices for engaging the threads of the tap while the inferior surfaces of the following threads compresses the cancellous material 34 of the bone against the concave surfaces of the helical threads, and against the core, thereby locking the screw into the bone. The inferior thread surfaces have varying angles, which displace the cancellous bone downwardly into the concave superior thread surfaces, and against the tapered core of the screw, to thereby increase the pull-out resistance of the screw.

Thus, the improved bone screw has at least one ledged thread at the tip of the screw with the following threads provided with sharp apices all the way to the head of the screw. Consequently, fractures of the bone as a result of corrupted screw threads adjacent to the screw head are eliminated.

As the screw 10 is inserted in the pilot hole created by a tap, it is rotated through the compact shell 32 and into the spongy cancellous material 34. The screw is then in the precise path of insertion. Thereafter, the screw threads following the initial ledged threads have sharp apices, which cut easily in the spongy cancellous material without pulling apart the interior of the bone. The cancellous material is thus compressed by the inferior threads 21 against the superior threads 20. Since the surface of the superior threads are concave, more cancellous material is pressed, compacted and held in the concave basin of each screw thread to firmly mechanically lock the screw in the bone, and to increase the bone's resistance to axial pull-out.

Figure 14:
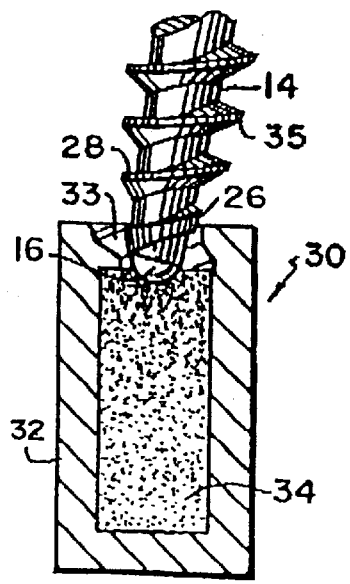
FIGS. 14–16 are side views of the bone screw being inserted incorrectly with FIG. 16 showing the ability to correct the bone screw insertion.
Figure 15:
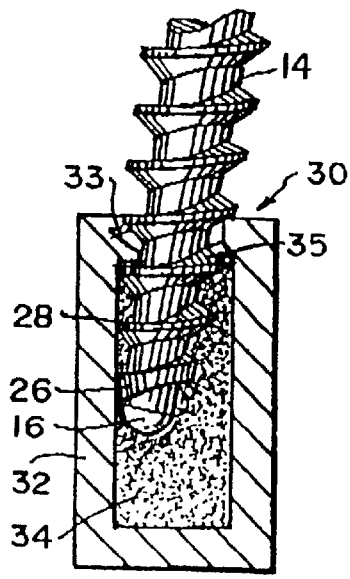
Figure 16:
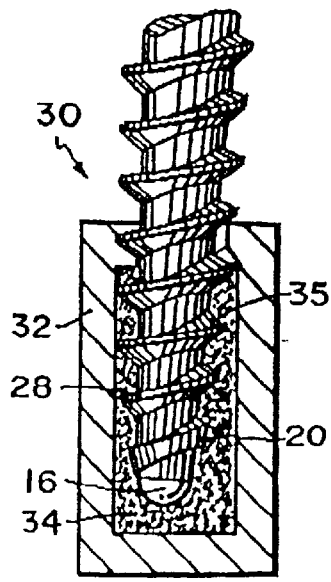

Referring now to FIGS. 14–16, the bone screw 10 is shown being applied to the bone after the compact shell is tapped at 33. In this instance the screw is inserted incorrectly at an angle which could result in serious injury to the spinal chord if it continues in its path of insertion. However, the surgeon performing the procedure cam remedy the incorrect path of insertion by withdrawing the bone screw and the tapped hole on the left of the screw shown in the drawings so that the screw when it is re-inserted as shown in FIG. 16 assumes the correct path of insertion.

Figure 10:
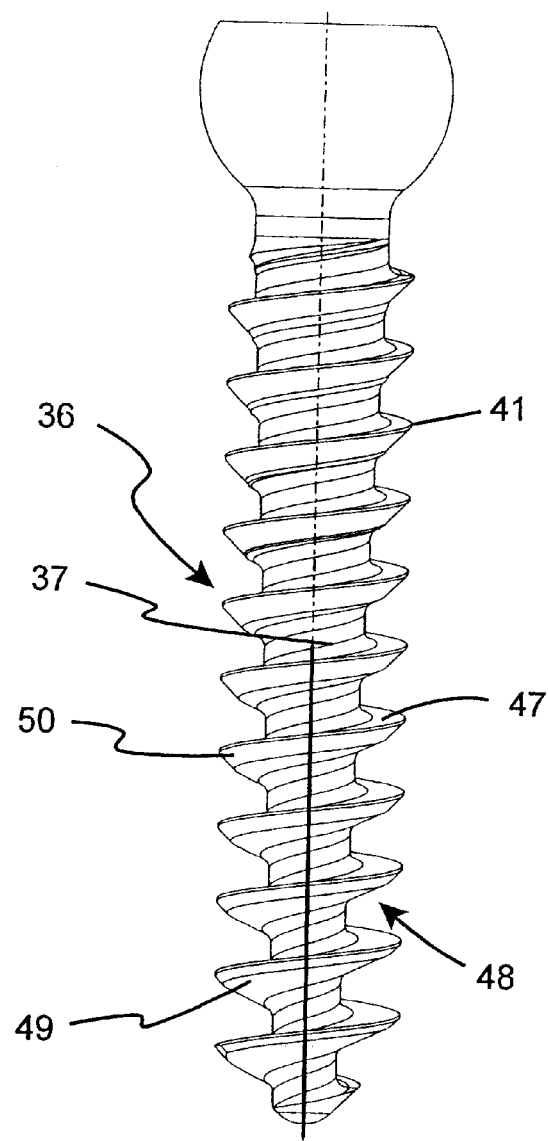
FIG. 10 is a front elevation view of an alternate embodiment of our invention showing the compound inferior thread surface.

Referring now to FIG. 10, an alternate embodiment of the present invention is shown in which the tapered bone screw is referred to generally by the reference numeral 36. In this embodiment all screw threads have sharp apices. The sharp apices are shown by a constant thread crest width 41. The tapered cylindrical core 37 is shown with the thickest part adjacent to the screw head. In this embodiment the helical screw threads have flat superior surfaces 47. The inferior surface 48 has a compound curve made up of an interior portion 49, with angle lambda, and an exterior portion 50, with angle e. The thread pitch h is substantially the same throughout the length. Because of the tapered core, the area between the threads decreases from the lead end toward the head. This configuration contributes to the compression of the bone between threads and increases pull-out forces.

The advantage of this embodiment is that the manufacturing process is much faster and less complex than the process required for the manufacture of the embodiment of FIGS. 1–9.

Figure 10A:
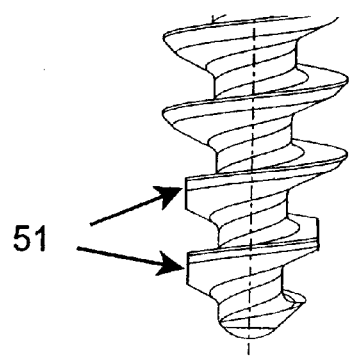
FIG. 10A is a front elevation of the embodiment of FIG. 10 showing ledged threads at the leading end.

FIG. 10A shows a leading end of the screw of FIG. 10. The ledged threads 51 have a smaller diameter than the remainder of the threads for preventing misalignment during use.

Figure 17:
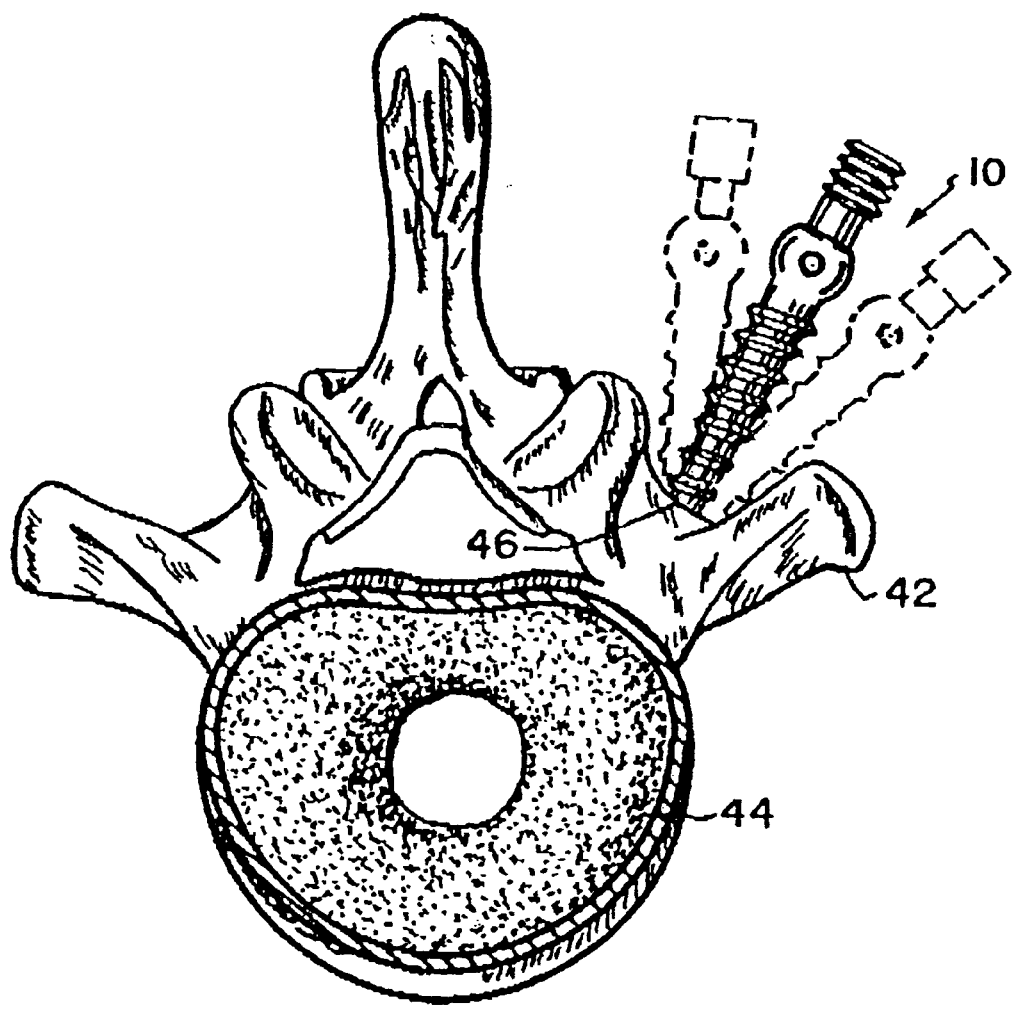
FIG. 17 is a perspective view of the bone screw of our invention being threaded into the isthmus of a vertebral pedicle.

FIG. 17 shows the pedicle 42, which is an isthmus of the vertical body 44. It should be noted that the pedicle isthmus is narrow at 46, which is the location for screw placement. As shown, the bone screw 10 in full lines is in the correct position. However, if the screw 10 is inserted by error in the location as shown in dotted lines serious neurological problems may result due to the proximity of the patient's spinal cord. Thus, it is imperative that the present procedure, utilizing a tap for bone screw placement, should be carefully followed with the screw thread arranged as described hereinbefore.

Figure 18:
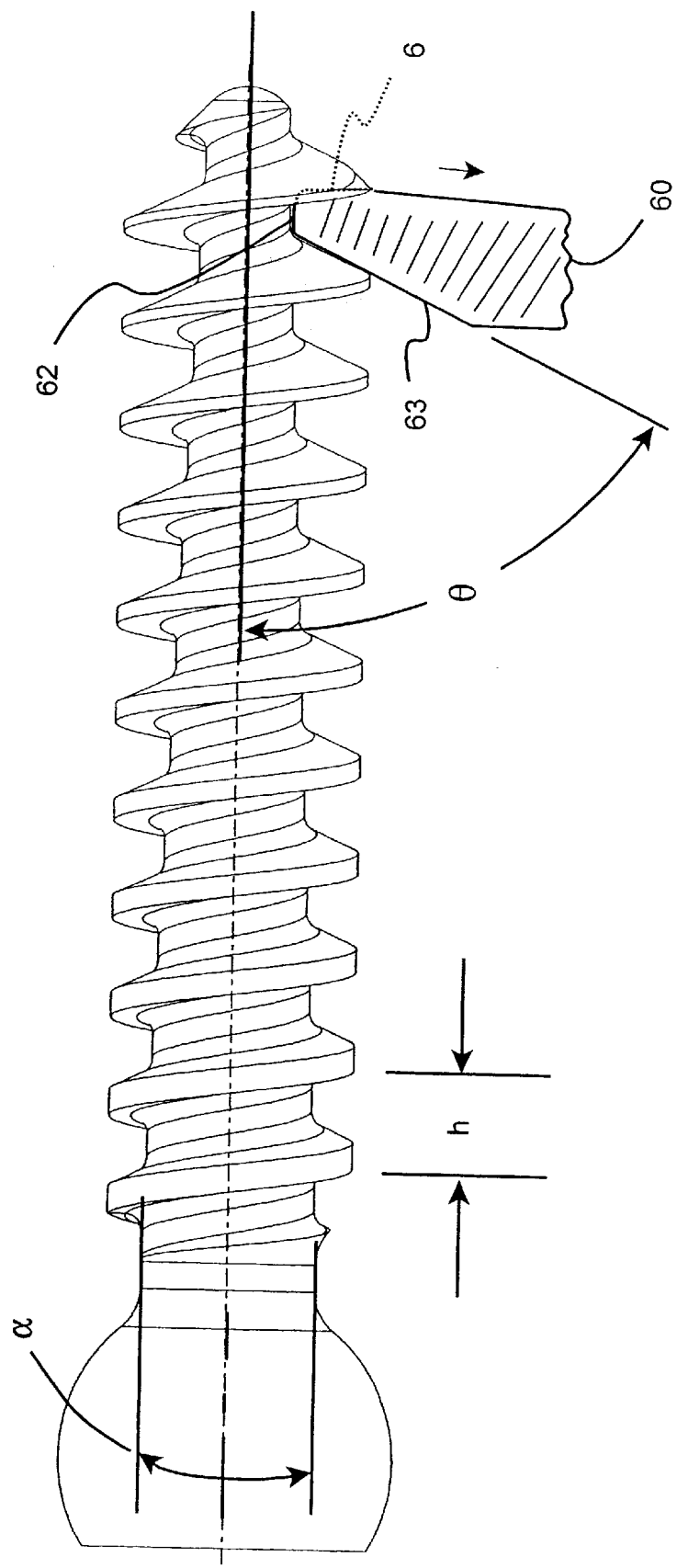
FIG. 18 is a perspective view with the tool bit in cross section of step 1 of the method of making the screw of FIG. 10.
Figure 19:
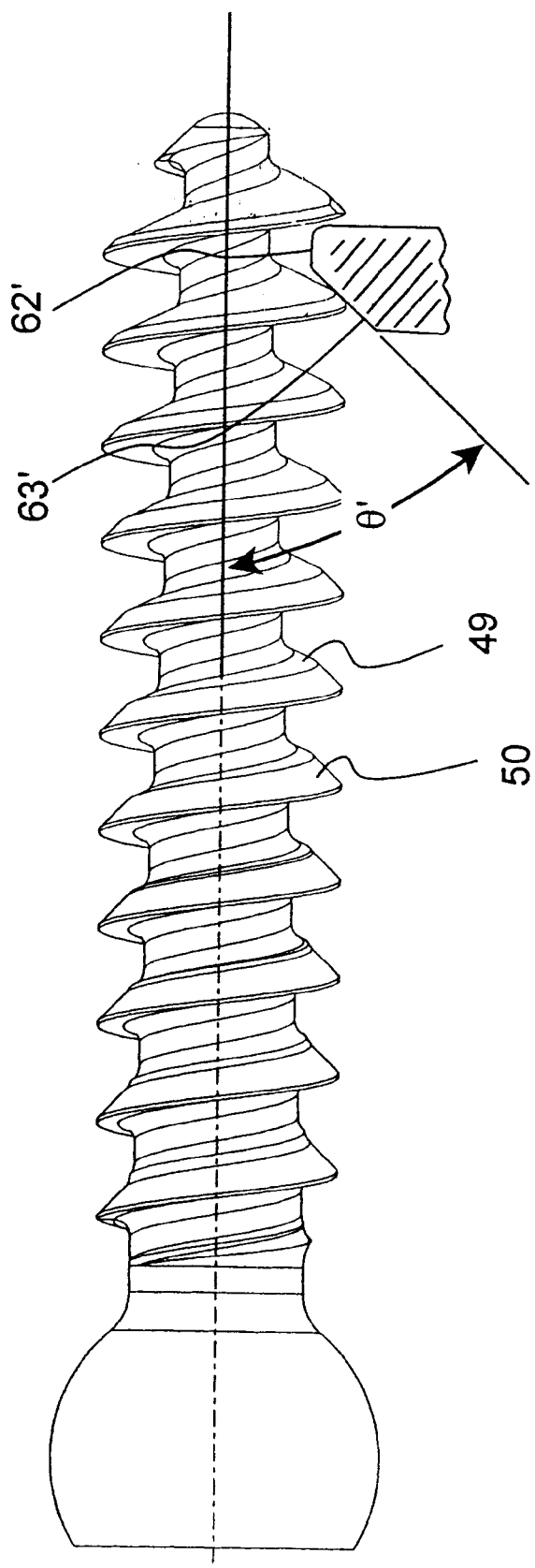
FIG. 19 is a perspective view with the tool bit in cross section of step 2 of the method of making the screw of FIG. 10.

FIGS. 18 and 19 show the apparatus and steps required to mass produce the bone screw of FIGS. 10–10A. The process starts with a conical or tapered core. The leading end is smaller with the shank or core becoming thicker toward the head of the screw. The angle of taper of the core, as shown, is a minor angle. The tool bit advances along the core or shank from the leading end toward the head. Because of the taper each successive thread that is cut in the shank will be thicker at the thread crest.

The tool bit 60 which makes the initial cut on the core is set at a particular distance from the longitudinal axis of the shank. The tool bit has a planar cutting surface 61 which forms the superior surface of the threads. The leading edge of the tool bit 62 has a cutting surface which establishes the thread pitch. Opposite the surface 61, the tool bit has an angled cutting surface 63. This angled surface makes the angle theta with the longitudinal axis of the screw core. As the core advances through the tool bit or the tool bit advances along the core, the screw threads that emerge are of fixed pitch, have a constant outside diameter, with a flat superior surface, an inferior surface with a fixed angle, a variable inside diameter and a variable crest width. The variation in inside diameter and thread crest width results from the relationship between the taper angle of the shank and the die angle theta.

The second tool bit, shown in FIG. 19, is substantially the same as the first tool bit in configuration. However, the second tool bit is set at a greater distance from the longitudinal axis of the shank. This is partly the result of die surface 62' being larger than the surface 62 of the first tool bit. The angled surface 63' forms a larger angle theta' with the longitudinal axis of the core. As the second tool bit completes the cut, the inferior surface of the threads are modified with a second outer portion 50 disposed at a different angle to the longitudinal axis of the core than the interior portion 49. This compound curve of the inferior surface results in a constant crest width throughout the length of the screw. The compound curve and the particular dimension of the constant crest width can be varied by varying the difference between the angles theta and theta'. A variation of about 20 degrees produces a particularly good result.

The screw made by the process shown in FIGS. 18 and 19 can have ledged leading threads, as shown in FIG. 10A, if desired. The starting cores could already have ledged leading threads or the ledged threads could be machined before the first step, between the first and second step or after the second step.

A bone screw according to the invention shown in FIG. 10 was submitted to The University of Miami School of Medicine for comparative testing. The instant screw was compared to the Isola 6.3 mm pedicle screw which is a well known bone screw of similar construction. This screw has straight-cut threads.

Each screw was inserted into cadaver pedicle and subjected to a pull out test. Each screw was completely inserted into the bone then subjected to a fatigue test of a plus or minus 20 N cyclic load applied at 90 degrees to the screw axis at 10 Hz for 250,000 cycles. The torque required to initiate removal was recorded. The screws were then fully inserted into cadaver pedicle to the torque already recorded.

A pullout force was directed along the axis of the screws to obtain the force required to fully remove each screw from its pedicle. The peak pullout force for the Isola 6.3 mm was 236.3 N. The peak pullout force for the screw of this invention was 637.9 N or approximately 270% greater than the prior art screw.

It is to be understood that while we have illustrated and described certain forms of our invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What is claimed is:

1. A method of making a screw comprising the steps of:
A) providing a tapered core having an initial diameter adjacent a large head end which tapers to a smaller diameter at a leading end;
B) providing a first tool bit at a first distance from the longitudinal axis of said core, said tool bit having a first cutting surface disposed at an acute angle to the longitudinal axis of said core;

C) making a first helical tool bit cut from the leading end toward the head end, said first helical tool bit cut producing a helical thread from said leading end to said head end with an inferior surface related to the angle between the first cutting surface of said first tool bit and the angle of taper of said tapered core;

D) providing a second tool bit at a second distance from said longitudinal axis of said core, said second tool bit having a second cutting surface disposed at an acute angle to the longitudinal axis of said core that is greater than said first angle; and E) making a second helical die cut from the leading end to said head end, said second helical tool bit cut producing a compound curve on said inferior surface of said helical thread and resulting in a sharp apice on said helical thread.

* * * * *